United States Patent
Bendix

(10) Patent No.: US 10,470,918 B2
(45) Date of Patent: Nov. 12, 2019

(54) OSTOMY WAFER

(71) Applicant: Coloplast A/S, Humlebaek (DK)

(72) Inventor: Jakob Bendix, Koebenhavn V (DK)

(73) Assignee: Coloplast A/S, Humlebaek (DK)

(*) Notice: Subject to any disclaimer, the term of this patent is extended or adjusted under 35 U.S.C. 154(b) by 365 days.

(21) Appl. No.: 15/313,979

(22) PCT Filed: May 28, 2015

(86) PCT No.: PCT/DK2015/050134
§ 371 (c)(1),
(2) Date: Nov. 25, 2016

(87) PCT Pub. No.: WO2015/180731
PCT Pub. Date: Dec. 3, 2015

(65) Prior Publication Data
US 2017/0224523 A1 Aug. 10, 2017

(30) Foreign Application Priority Data
May 28, 2014 (DK) .................................. 2014 70311

(51) Int. Cl.
*A61F 5/443* (2006.01)
*A61F 5/445* (2006.01)

(52) U.S. Cl.
CPC .............. *A61F 5/443* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 4,762,738 A | * | 8/1988 | Keyes | A61F 5/445 428/34.3 |
| 5,636,643 A | * | 6/1997 | Argenta | A61M 1/0088 128/897 |
| 6,099,508 A | * | 8/2000 | Bousquet | A61M 39/0247 128/DIG. 26 |
| 7,708,724 B2 | * | 5/2010 | Weston | A61M 1/0088 604/304 |
| 9,078,990 B1 | * | 7/2015 | Obst | A61M 27/00 |
| 2007/0066946 A1 | * | 3/2007 | Haggstrom | A61M 1/0031 604/313 |
| 2008/0161778 A1 | * | 7/2008 | Steward | A61M 1/0088 604/543 |
| 2008/0287892 A1 | * | 11/2008 | Khan | A61F 5/449 604/313 |

(Continued)

FOREIGN PATENT DOCUMENTS

| | | |
|---|---|---|
| CN | 103561693 A | 2/2014 |
| CN | 103582506 A | 2/2014 |

(Continued)

*Primary Examiner* — Tatyana Zalukaeva
*Assistant Examiner* — Guy K Townsend
(74) *Attorney, Agent, or Firm* — Coloplast Corp., Coloplast A/S; Nick Baumann

(57) ABSTRACT

Disclosed is an ostomy wafer comprising a central peristomal area surrounding a stoma receiving hole, from which a plurality of petals are extending radially, the petals being interconnected via bridges with a apex pointing away from the central area. The wafer is suitable for application to especially demanding skin surface conditions, such as in ostomists suffering from hernia.

13 Claims, 2 Drawing Sheets

(56) References Cited

U.S. PATENT DOCUMENTS

| | | | | |
|---|---|---|---|---|
| 2009/0131893 A1* | 5/2009 | Priest | ................... | A61F 5/4408 604/342 |
| 2009/0192467 A1* | 7/2009 | Hansen | ............. | A61B 17/3462 604/174 |
| 2009/0209917 A1* | 8/2009 | Tanaka | ................... | A61K 9/007 604/174 |
| 2010/0145293 A1* | 6/2010 | Verhaalen | ............... | A61F 5/445 604/337 |
| 2010/0262095 A1* | 10/2010 | Hall | ................... | A61M 1/0084 604/319 |
| 2012/0101458 A1* | 4/2012 | Hall | ....................... | A61F 5/445 604/319 |
| 2012/0143155 A1* | 6/2012 | Edvardsen | ............ | A61F 5/4404 604/318 |
| 2014/0114265 A1* | 4/2014 | Israelson | ................ | A61F 5/443 604/342 |
| 2016/0120687 A1* | 5/2016 | Obst | ....................... | A61F 5/443 604/337 |
| 2017/0143535 A1* | 5/2017 | Praame | ................... | A61F 5/445 |
| 2017/0224523 A1* | 8/2017 | Bendix | ................... | A61F 5/445 |
| 2018/0021164 A1* | 1/2018 | Fenton | ................... | A61F 5/445 604/336 |
| 2018/0021165 A1* | 1/2018 | Fenton | ................... | A61F 5/445 604/338 |
| 2018/0104089 A1* | 4/2018 | Nyberg | ................... | A61F 5/445 |
| 2018/0235801 A1* | 8/2018 | Oellgaard | ............. | A61F 5/4404 |

FOREIGN PATENT DOCUMENTS

| | | | | |
|---|---|---|---|---|
| DK | 96019 | C * | 5/1963 | ............. A61F 5/445 |
| DK | 96019 | C | 5/1963 | |
| EP | 0882437 | A2 * | 12/1998 | ............. A61F 5/445 |
| EP | 0882437 | A2 | 12/1998 | |
| EP | 1269946 | A1 * | 1/2003 | ............. A61F 5/445 |
| EP | 1269946 | A1 | 1/2003 | |
| EP | 1541180 | A2 | 6/2005 | |
| GB | 2311467 | A1 | 10/1997 | |
| RU | 2220685 | C1 | 1/2004 | |
| WO | 2009006901 | A1 | 1/2009 | |
| WO | 2012163994 | A1 | 12/2012 | |

* cited by examiner

OSTOMY WAFER

The invention relates to an ostomy wafer for use in an ostomy appliance, in particular, the invention relates to ostomy wafers for ostomies or stomas located on a bulge or hernia on the skin surface of a user.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive wafer for attachment to the human skin. Alternatively, the ostomy appliance may be a two-piece appliance comprising a wafer and a collecting bag which may be coupled to and uncoupled from each other through a coupling means. This has the effect that the wafer does not need to be separated from the skin of the user as often as exchange of the collecting bag requires. The wafer may need often only to be changed every third or fourth day depending on the user, whereas the collecting bag may be changed more than once per day. Typically, it is desirable to need as few exchanges of the wafer as possible in order to reduce the risk of skin complications.

One of the main concerns of ostomates using ostomy appliances having an adhesive wafer for attachment to the skin surrounding a stoma, and where a collecting bag is attached to the wafer for collecting stoma output, is that the ostomy adhesive attachment may be compromised resulting in leakage or even complete detachment of the ostomy appliance.

Numerous attempts have been made to solve this problem and even though some attempts have been partly successful, still there exist no products which completely solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma, for local irregular skin topography and combinations of all of the above.

Particularly in relation to persons suffering from hernia, i.e. the phenomenon that a bodily structure (e.g. the intestine) protrudes through a rupture in smooth muscle tissue surrounding it, experience shows that it is often very difficult to attach an ostomy appliance to the skin surface where the hernia is located in a manner that provides satisfactory protection against leakage from stomal fluids. It is not uncommon that the surgical procedure undertaken to make a stoma on a patient also results in a weakening of the muscle tissue of the stomach wall which may consequently lead to the formation of a hernia where the stoma is located on the skin surface (or close or adjacent to the stoma).

Moreover, a hernia is not a static phenomenon. It is almost certain never to take a perfect geometrical shape but instead often has a highly irregular topography. This may be caused by many factors such as conditions in the physical surroundings of the user, level of activity of the user and contents of the bowels at any given time, just to mention a few.

In addition to the formation of hernias, other physical conditions or pathologies may also mean or lead to irregular skin topography such as bulges or otherwise "hilly" stomach skin surface, the causes including e.g. trauma and/or obesity.

DESCRIPTION OF RELATED ART

GB2311467 describes an ostomy appliance comprising a collection pouch and an adhesive flange coupled to the pouch for securing the appliance with respect to the skin of a wearer. The adhesive flange has an aperture which communicates with an interior of the pouch and the flange comprises a plurality of fingers which extend away from the aperture. The document also describes an adhesive flange for an ostomy appliance.

Wafers with a flower shaped outline such as disclosed in GB2311467 may more easily be fitted around a bulgy stoma due to the fingers. However, in the part of the outline connecting the fingers, wrinkles may occur when fitted to curved surfaces. If such wrinkles become too large or turn into deep folds, they may give rise to leakage.

SUMMARY OF THE INVENTION

The present invention provides an adhesive wafer to be used as part of or with an ostomy appliance. Particularly, the invention provides a solution to minimize the risk of leakage under the wafer when applied to an irregular or bulgy skin area. The wafer is especially advantageous to be used on users suffering from and having their stoma located on a non-planar and non-regular skin surface.

DETAILED DESCRIPTION OF THE INVENTION

Figure 1:
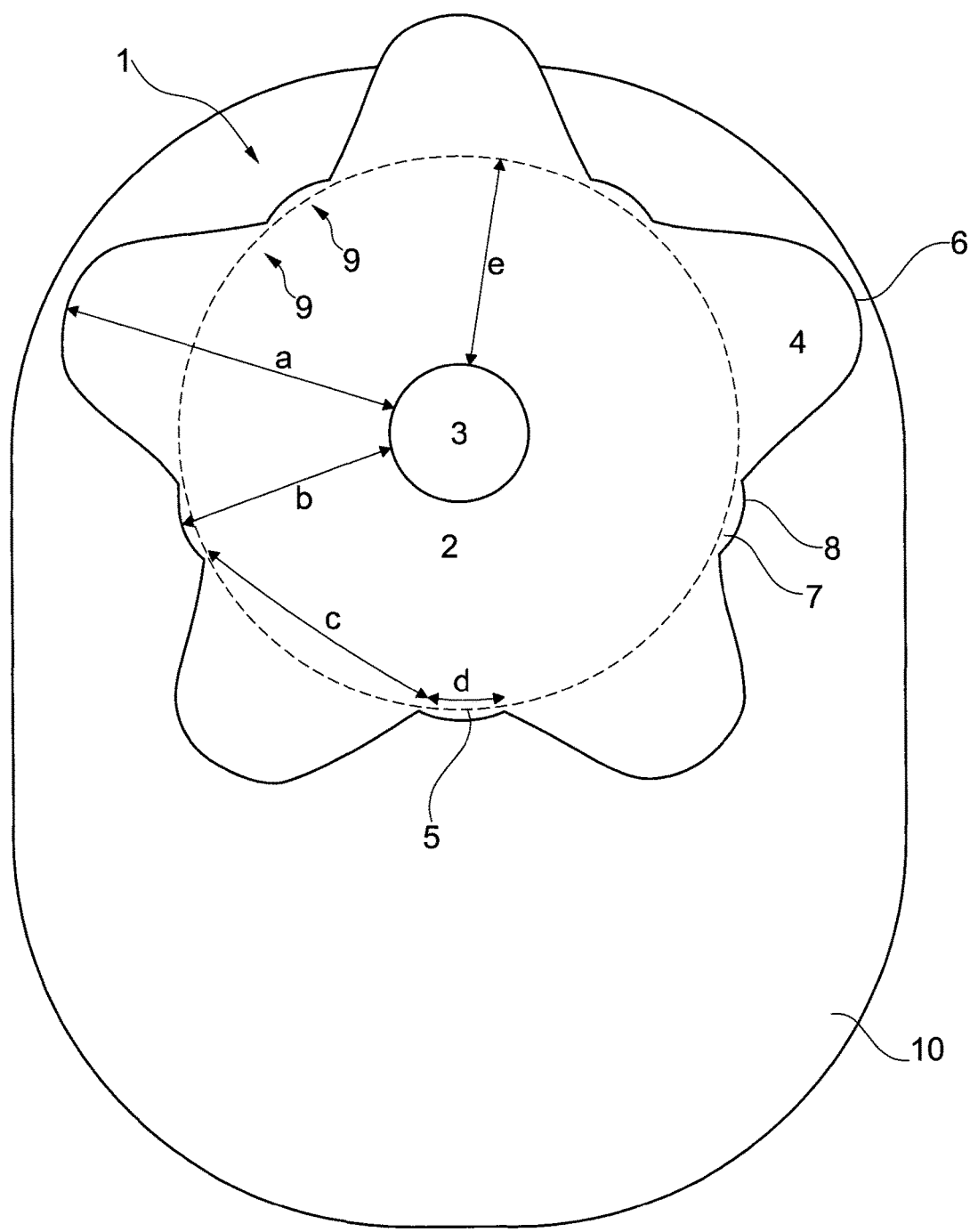
FIG. 1 is a schematic view of an ostomy wafer according to embodiments of the invention.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus the axial direction is substantially perpendicular to the abdominal surface of the user.

The radial direction, or radially, is defined as transverse to the axial direction that is transversely to the direction of the stoma.

"Release liner" is intended to define a liner covering the proximal (skin contacting) side of the skin-friendly adhesive, that ensures at least that the properties of the adhesive are preserved and that the adhesive surface is not laid open until just before the use.

"Peristomal skin surface" is intended to define an area of the skin surface adjacent to and surrounding the stoma. The extent of the area may be considered to correspond approximately to a skin surface area covered by at least a first section of the ostomy wafer—the first section then being closer to the stoma than a second section.

"Petal" is intended to define a portion of the wafer extending radially from the central area of the wafer, like the petals of a flower. The petals act as fingers or flaps that can be fitted around a protruding body part. The petal may end in an apex being rounded, angular or pointy.

"Bridge" is intended to define the part of the wafer connecting two neighbouring petals.

By "centre" or "central" is addressed the stoma receiving hole or the area surrounding the hole. I case the wafer is symmetric the centre will be equal to the mathematically defined centre. However, asymmetric wafers may occur, having the hole placed eccentric with regard to the mathematically defined centre.

By "convex" is herein meant a curved line arching away from point of origin. Thus, the start point and the end point of the line is closer to the point of origin than the middle portion of the line. In the same way is "concave" defined as a line arching towards the point of origin. If nothing else is stated, the point of origin is the central area/stoma receiving hole of the wafer.

In a first aspect, the invention relates to an ostomy wafer comprising:
a central peristomal area surrounding a stoma receiving hole, the central peristomal area is continuous and extends a first radial distance from a periphery of the stoma receiving hole to define a continuous band of material around the stoma receiving hole;
a first petal spaced apart from a second petal, each of the first petal and the second petal extends away from the continuous band of material, the first petal has a first petal length measured from the stoma receiving hole to an apex of the first petal and the second petal has a second petal length measured from the stoma receiving hole to an apex of the second petal; and
a bridge located between the first petal and the second petal, the bridge extends away from the continuous band of material and has a bridge length measured from the stoma receiving hole to an apex of the bridge;
wherein the bridge length is less than the first petal length and the second petal length.

The apex of the first petal may be convex and the apex of the second petal may be convex and the bridge may have a base forming a first concave segment with the first petal and a second concave segment with the second petal. The bridge may form two concave regions between the first petal and the second petal.

In one embodiment of the invention, the first petal and the bridge meets in an angle instead of in a concave region.

The bridge may comprise a central convex portion, connected to the neighbouring petals by a concave section. In embodiments, the bridge may comprise two or more convex portions, separated by concave sections.

The wafer may be provided with at least three petals, such as four petals, five petals or even six petals.

The petals may have the same length or the petal length may vary. The length of the petals may be substantially larger than the length of the bridge.

The petal length can be divided into the length (radius) of the central area plus the length of the extending petal. In the same way, the length of the bridge may be divided into the length of the central area (radius) plus the length of the extending bridge. The length of the extending petal may be at least twice the length of the extending bridge, such as at least three times, four times or event at least five times the length of the extending bridge.

The length of the extending bridge may be at least 5%, such as at least 6%, 7%, 8%, 9% or even at least 10% of the length of the extending petal.

In embodiments, the length of the extending bridge is at least 1 mm, such as at least 1.2 mm, 1.3 mm, 1.4 mm, 1.5 mm, 1.6 mm, 1.7 mm, 1.8 mm, 1.9 mm or even at least 2 mm.

The apex of the bridge may be convex.

In one aspect, the invention relates to an ostomy wafer comprising:
an outer periphery formed by a plurality of petals extending away from a central area; and
a bridge formed between adjacent petals of the plurality of petals;
a stoma receiving hole formed at a centre of the central area, where the central area forms a continuous band of material around the stoma receiving hole;
wherein each of the plurality of petals has a petal length extending from the stoma receiving hole to a petal apex and the bridge has a bridge length extending away from the stoma receiving hole to an apex of the bridge, with the bridge length being less than the petal length.

In another aspect, the invention relates to an ostomy wafer comprising:
a stoma receiving hole formed at a centre of the wafer and a central area formed as a continuous band of material around the stoma receiving hole;
an outer periphery of the wafer is formed by a plurality of petals extending away from the central area; and
a plurality of bridges, each bridge formed between adjacent petals of the plurality of petals, with each bridge having a bridge width measured between the adjacent petals of the plurality of petals and each of the plurality of petals having a petal width measured between two of the plurality of bridges;
wherein and the bridge width is less than the petal width.

Each of the plurality of petals has a petal length measured from the stoma receiving hole to an apex of the petal and the bridge has a bridge length measured from the stoma receiving hole to an apex of the bridge, with the bridge length may be less than the petal length.

The width of the petals may be at least the double of the width of the bridge or even at least three times the width of the bridge.

The radially extending petals may be spaced apart equidistantly around the circumference of the centre area.

By the invention, a number of advantageous effects are achieved. First of all, a user having a stoma located on a bulge or hernia, or on an otherwise "hilly" topographic skin surface, has improved control of the product application procedure.

By introducing bridges between the petals, the formation of a single large fold or wrinkle between the petals is prevented. Instead, minor wrinkles may be created on each side of the bridge—in the concave areas or at the angle. However these wrinkles are smaller than the single large wrinkle and will not extend far towards the centre of the wafer as well as they will not be as deep and is thus less susceptible to introducing a route for leakage in the wafer.

The material of the bridge may be thicker than the thickness of the petals. The enhanced thickness may be achieved by a thicker layer of adhesive. Whereas one would expect a smaller thickness of the bridge would result in creation of smaller/less wrinkles, it has surprisingly been shown that a thicker layer of material in the bridge area may be better able to "absorb" the wrinkle by compacting the material instead of creating a proper fold. When wrinkles becomes smaller, they tend to be absorbed and disappear.

The skin facing adhesive layer of the ostomy wafer may comprise any suitable adhesive. The adhesive may comprise absorbent particles such as hydrocolloids. The distal surface of the wafer may be provided with a backing layer.

The wafer may comprise at least one adhesive. In embodiments, the wafer may comprise two or more adhesives, for example a first adhesive at the central portion and a second adhesive at the edge portion. This disposition of the first and second adhesive effectively provides an ostomy base plate wherein the first adhesive having one set of characteristics covers the peristomal area, and the second adhesive having another set of characteristics covers the skin surface around (radially beyond) the peristomal skin surface.

In embodiments, the adhesive may comprise a skin-friendly pressure sensitive adhesive composition suitable for medical purposes comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions reference is made to applicant's granted European patent EP1541180B1.

In embodiments, the adhesive is elastic. The second adhesive may be more or may be less elastic than the first adhesive or the two adhesives may even have identical elasticities if desired.

In embodiments, the adhesive comprises a polar plasticising oil or a combination of polar plasticising oils in the content of above 10% (w/w) of the final adhesive, and at least one polar polyethylene copolymer, wherein the content of the polyethylene copolymer is 10-50% (w/w) of the final adhesive, the polyethylene copolymer has a melt flow index below 2 g/10 min (190° C./21.1N).

In embodiments, polymers that may be used for the adhesive may be copolymers of ethylene and a polar monomer. The copolymers typically comprise less than about 70% ethylene, have water vapor transmission of more than 50 g/m2/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapor transmission of more than 50 g/m2/day for a 150 μm sheet when measured according to MVTR Test Method (inverted cup method).

In embodiments, the adhesive may comprise polar oils, generally being those that have good solubility in the polar domains of the polymer, i.e. provide softness without sacrificing too much tensile strength of the polymer. Oils that can support good water vapor permeability are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene. Further information on the types of adhesives suitable for the adhesive disclosed in these embodiments is available in applicant's published application WO 2009/006901A1.

The wafer may be provided with coupling means for attaching a collection bag to the wafer (two-piece device) or a collection bag may be permanently attached to the wafer (one-piece device).

During use, the collecting bag is secured to the adhesive wafer. Thus in one embodiment, the ostomy appliance is a one-piece ostomy appliance in which the collecting bag is permanently secured to the adhesive wafer, for example by adhesive or welding. In the latter embodiment, the collecting bag may be integrated with the wafer.

In another embodiment, the collecting bag and the adhesive wafer form a two-piece ostomy appliance which is delivered to the user in two pieces that must be connected to each other by the user. The collecting bag may be secured to the adhesive wafer by means of an adhesive provided between the collecting bag and the adhesive wafer. The latter adhesive may be provided on the opposite side of the adhesive wafer than the skin facing adhesive layer. Alternatively, or as a supplement, the collecting bag may be coupled to the adhesive wafer by means of a mechanical coupling means.

In one embodiment, the shape of the central area of the adhesive wafer is substantially round such as circular or oval. The stoma receiving hole may be located asymmetrically or centrally of the wafer.

The skin facing adhesive layer may be covered by a release liner. The release liner may be siliconised or otherwise provided with a non-stick surface on the side which faces the skin facing adhesive layer. The release liner may be in one piece or it may be in two or more pieces, facilitating stepwise application. This release liner must be removed in order for the user to adhere the skin facing adhesive layer to the skin of the user and does not form a part of the invention.

The edge portion of the wafer may be beveled in order to provide a smooth transition to the skin and avoid rolling up of the edges.

DETAILED DESCRIPTION OF THE DRAWING

Initially, it shall be noted that the figures are schematic illustrations intended only to address the principles and functions of the wafer according to the invention and are not to be considered limiting to the scope of the attached claims. Furthermore, the figures and particularly the individually illustrated elements are not necessarily to scale, neither individually nor in relation to each other.

FIG. 1 shows a schematic view of an ostomy wafer 1 according to the invention, seen from the skin-facing side. The wafer 1 comprises a central area 2 in the form of a continuous band of material surrounding a stoma receiving hole 3, the central area outer periphery being indicated by the dotted line 5 and having a radial width e. Five petals 4 are extending radially from the central area. The petals comprises a convex apex 6. Between neighbouring petals 4, a bridge 7 is extending from a first petal to a second petal. The bridge 7 is provided with a convex apex 8 being connected to the neighbouring petals 4 by a concave portion 9. The wafer is shown connected to a collection bag 10. The length of the petals 4 are indicated as the line a running from the stoma receiving hole 3 to the apex 6 of the petal 4. The length of the bridge 7 is indicated as the line b, extending from the stoma receiving hole 3 to the apex of the bridge 8. The width of the petal 7 is indicated by the line c extending from one bridge 7 to the next bridge 7 and the width of the bridge 7 is indicated by the line d extending from the first petal 4 to the next petal 4. The petals 4 extends radially from the stoma receiving hole 3 to define an area projecting from the outer periphery 5 of the central area 2. In the same way is the bridge 7 projecting from the outer periphery 5 but the projection of the bridge 7 is much smaller than the projection of the petal 4.

Figure 2:
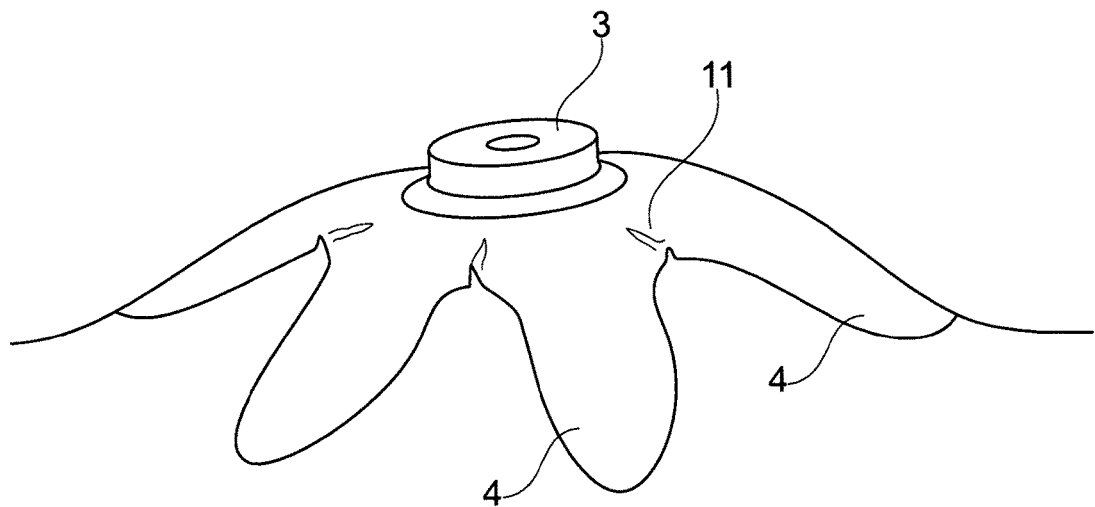
FIG. 2 is a view of a prior art ostomy wafer mounted on protruding skin around a stoma.

FIG. 2 shows a view of a wafer according to prior art being mounted on a protruding peristomal area. In the area between neighbouring petals 4, being a concave line, a single wrinkle 11 is typically formed. The wrinkle 11 may be quite large and extend radially from the edge of the wafer and pointing towards the stoma receiving hole 3. Such wrinkle 11 is inclined to provide a route for leakage.

Figure 3:
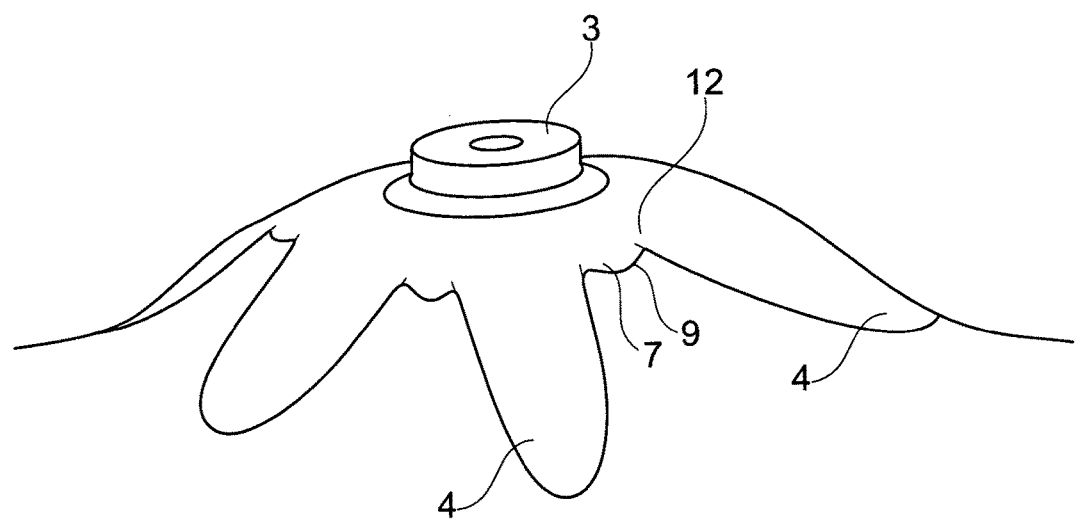
FIG. 3 is a view of ostomy wafer according to embodiments of the invention, mounted on protruding skin around a stoma.

FIG. 3 shows a view of an embodiment of the invention being mounted on a protruding peristomal area analogous to the prior art wafer of FIG. 2. The bridge 7 prevents formation of one single wrinkle between the neighbouring petals 4, instead minor wrinkles 12, if any, is formed in the concave area 9 connecting the bridge 7 to the petals 4.

The invention claimed is:

1. An ostomy wafer comprising:
 a central peristomal area surrounding a stoma receiving hole, wherein the central peristomal area is continuous and extends a first radial distance from a periphery of the stoma receiving hole to define a continuous band of material around the stoma receiving hole;
 a first petal spaced apart from a second petal, each of the first petal and the second petal extends away from the continuous band of material, the first petal has a first petal length measured from the stoma receiving hole to an apex of the first petal and the second petal has a second petal length measured from the stoma receiving hole to an apex of the second petal; and
 a bridge located between the first petal and the second petal, the bridge is continuous with and extends away from the continuous band of material, wherein the bridge is formed as a radial projection from the central peristomal area to define a bridge length measured from the stoma receiving hole to an apex of the bridge;
 wherein each of the first petal length and the second petal length is at least a factor of 2 times greater than the bridge length to configure the bridge to prevent wrinkle formation in wafer material between the first petal and the second petal.

2. The ostomy wafer of claim 1, wherein the apex of the first petal is convex and the apex of the second petal is convex and the bridge has a base forming a first concave segment with the first petal and a second concave segment with the second petal.

3. The ostomy wafer of claim 1, wherein the bridge forms two concave regions between the first petal and the second petal.

4. The ostomy wafer of claim 1, wherein the first petal and the bridge meet in an angle.

5. The ostomy wafer of claim 1, wherein the apex of the bridge is convex.

6. The ostomy wafer of claim 1, wherein the central peristomal area is substantially circular or oval.

7. The ostomy wafer of claim 1, wherein the wafer comprises at least three petals.

8. The ostomy wafer of claim 1, wherein the wafer comprises at least five petals.

9. The ostomy wafer of claim 1, wherein the first petal length is substantially the same as the second petal length.

10. The ostomy wafer of claim 1, wherein a width of each of the first petal and the second petal is at least a factor of 2 wider than a width of the bridge.

11. The ostomy wafer of claim 7, wherein the at least three petals are equidistantly spaced apart around a circumference of the central peristomal area.

12. The ostomy wafer of claim 1, wherein the first petal has a first petal thickness and the second petal has a second petal thickness, and a thickness of the bridge is greater than the first petal thickness and greater than the second petal thickness.

13. The ostomy wafer of claim 1, further comprising:
 a first adhesive attached to the central peristomal area; and
 a second adhesive attached to the first petal and to the second petal;
 wherein the first adhesive is different from the second adhesive.

* * * * *